(12) United States Patent  
Shimada et al.

(10) Patent No.: US 7,524,297 B2  
(45) Date of Patent: Apr. 28, 2009

(54) WALKING ASSISTANCE DEVICE PROVIDED WITH A FORCE SENSOR

(75) Inventors: Kei Shimada, Wako (JP); Takashi Hirata, Wako (JP); Jun Ashihara, Wako (JP); Tatsuya Noda, Wako (JP); Yasushi Ikeuchi, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 587 days.

(21) Appl. No.: 11/220,737

(22) Filed: Sep. 7, 2005

(65) Prior Publication Data

US 2006/0052732 A1 Mar. 9, 2006

(30) Foreign Application Priority Data

Sep. 8, 2004 (JP) ............................. 2004-260483  
Sep. 10, 2004 (JP) ............................. 2004-263283

(51) Int. Cl.  
*A61F 5/00* (2006.01)

(52) U.S. Cl. ............................. 602/16; 602/23; 602/26

(58) Field of Classification Search ............. 602/5, 602/16, 23, 26, 27  
See application file for complete search history.

(56) References Cited

U.S. PATENT DOCUMENTS

| | | | | |
|---|---|---|---|---|
| 5,662,693 A * | 9/1997 | Johnson et al. | ............... | 607/49 |
| 2003/0023195 A1 * | 1/2003 | Rahman et al. | ............... | 602/20 |
| 2005/0043661 A1 * | 2/2005 | Nashner | ............... | 602/26 |
| 2005/0251079 A1 * | 11/2005 | Carvey et al. | ............... | 602/26 |

FOREIGN PATENT DOCUMENTS

| | | |
|---|---|---|
| JP | 58-163364 | 9/1983 |
| JP | 7-163607 | 6/1995 |
| JP | 2000-107213 | 4/2000 |
| JP | 2000-227373 | 8/2000 |
| JP | 2001-331271 | 11/2001 |
| JP | 2003-220102 | 8/2003 |
| JP | 2003-250844 | 9/2003 |

* cited by examiner

*Primary Examiner*—Kim M Lewis  
(74) *Attorney, Agent, or Firm*—Rankin, Hill & Clark LLP

(57) ABSTRACT

In walking assistance device, a force detector (21) is provided between thigh retaining member (9) that directly retain the thigh of the user and a thigh support member (2) that is actuated by an actuator (TA1) provided in hip coupling portion. Thereby, the load acting on the hip coupling portion can be accurately detected, and the output of the force detector can be favorably used for the purpose of controlling the actuator so as to minimize the force that is applied to the thigh of the user. In particular, to the end of providing a suitably rigidity to the thigh retaining member so that the force produced by the actuator may be evenly applied to the entire thigh, and facilitating the effort required for the wearer to wear the walking assistance device, the thigh retaining member comprises a base portion (9a) connected to the thigh support member and two pairs of resilient arms (9b, 9c) extending laterally from either side of the base portion so that the thigh retaining member generally defines a shape of letter-C in plan view.

12 Claims, 7 Drawing Sheets

WALKING ASSISTANCE DEVICE PROVIDED WITH A FORCE SENSOR

TECHNICAL FIELD

The present invention relates to a walking assistance device including a force sensor provided between a member for retaining a thigh or leg of a user and the corresponding support member of the device so that the output signal from the force sensor may be used for the control of the device in a favorable manner.

BACKGROUND OF THE INVENTION

Various muscle assistance devices have been proposed as can be found in Japanese patent laid open publications No. 2003-250844 and No. 7-163607, for instance, for the purpose of providing an assisting force to the movement of the leg by using a torque actuator consisting of an electric motor or the like attached to a side part of the hip or knee joint. For instance, such a muscle assistance device enables a person caring a bedridden person to produce a force of the leg which is substantially greater than that the person is normally capable of producing or a person having a walking impediment owing to aging or the like to walk on his or her feet.

In the power assist devices disclosed in these Japanese patent laid open publications, the thigh of the user is secured to a rigid thigh support member in the form of an exoskeltal beam by a fastening belt which is connected to the thigh support member and wrapped around the thigh of the user. The leg of the user is similarly secured to the leg support member.

In Japanese patent laid open publication No. 2003-250844, the movement of the thigh of the user is detected by using a sensor provided between the belt fastener for securing the thigh to the thigh support member and the front surface of the thigh and other sensors that are provided in the toe and ankle. The drive force of the torque actuator is controlled according to the output electric signals of these sensors so as to assist the flexing movement of the thigh.

However, according to this prior art, the force sensor is provided between the thigh and the fastening belt wrapped around the thigh. Therefore, the belt has to be securely fastened around the thigh for an accurate measurement, but this prevents free movements of the muscles of the thigh, and causes a discomfort to the user. This prior art also includes force sensors placed under the sole of each foot, but these sensors provide limited information for the control of the walking assistance device.

Also, the fastening belt is intrinsically pliant and flexible, and this is advantageous as it can readily conform to the thigh which may differ significantly from one person to another, but the fastening belt is not capable of uniformly transmitting the force from the thigh support member to the thigh. Typically, the transmitted force concentrates at the point of connection between the fastening belt and thigh support member so that the adjacent part of the thigh is subjected to a localized force, and this is detrimental in transmitting a large force to the thigh and preventing discomfort to the user.

Also, the fastening and unfastening of such a belt is not convenient particularly because the fastening belt must be tautly applied to the thigh of the user and this requires a significant amount of effort.

BRIEF SUMMARY OF THE INVENTION

The present invention was made in view of such problems of the prior art, and a primary object of the present invention is to provide a walking assistance device including a force sensor which can provide data suitable for the control of the walking assistance device.

A second object of the present invention is to provide a walking assistance device including a force sensor which would not hamper the movement of the user.

A third object of the present invention is to provide a walking assistance device including a force sensor which can be worn by a user with comfort.

A third object of the present invention is to provide a walking assistance device including a force sensor which is easy to wear.

To achieve such an object, the present invention provides a walking assistance device, including; a pelvis support member adapted to be worn by a pelvis of a user; a thigh support member having an upper end pivotally connected to the pelvis support member via a hip coupling portion and provided with a thigh retaining member; a leg support member having an upper end pivotally connected to a lower end of the thigh support member via a knee coupling portion and provided with a leg retaining member; an actuator provided at least in one of the hip coupling portion and knee coupling portion for applying an assisting torque to the two members that are joined by the coupling portion; and a force detector provided between the thigh retaining member and thigh support member when the actuator is provided in the hip coupling portion or between the leg retaining member and leg support member when the actuator is provided in the knee coupling portion.

The actuator may be provided in the hip coupling portion to apply an assisting torque between the pelvis support member and thigh support member, and the force detector may be provided between the thigh retaining member and thigh support member. Preferably, the thigh support member includes an axially elongated rod member, and the thigh retaining member is connected to the thigh support member in an axially slidable manner.

Alternatively or additionally, the actuator may be provided in the knee coupling portion to apply an assisting torque between the thigh support member and leg support member, and the force detector may be provided between the leg retaining member and leg support member. Preferably, in this case, the leg support member includes an axially elongated rod member, and the leg retaining member is connected to the leg support member in an axially slidable manner.

Because the retaining member that directly engages the thigh or leg of the user is attached to the corresponding support member via a force detector, the load acting on the corresponding coupling portion can be accurately detected, and the output of the force detector can be favorably used for the purpose of controlling the actuator so as to minimize the force that is applied to the thigh or leg of the user. Preferably, the force detector is capable of detecting a force of any direction, and, for instance, may comprise a plate member having a cross shaped part having four arms defined by four L-shaped cuts and a strain sensor attached to each of the four arms.

According to a preferred embodiment of the present invention, the walking assistance device further comprises a foot support member having an upper end pivotally connected to a lower end of the leg support member via an ankle coupling portion. In this case, if an additional force detector is provided in the ankle coupling portion to detect a load acting between the leg support member and foot support member, it is possible to favorably carry out a control process for canceling the weight of the walking assistance device that is applied to the wearer by using the output from such a sensor.

To the end of providing a suitably rigidity to the thigh retaining member so that the force produced by the actuator may be evenly applied to the entire thigh, and facilitating the effort required for the wearer to wear the walking assistance device, the thigh retaining member may comprise a base portion connected to the thigh support member and at least a pair of resilient arms extending laterally from either side of the base portion so that the thigh retaining member generally defines a shape of letter-C in plan view. A similar arrangement may be used for the leg retaining member to a similar effect.

Preferably, the thigh retaining member comprises two pairs of resilient arms extending laterally from either side of an upper end of the base portion and from either side of a lower end of the base portion, respectively, and the thigh retaining member extends over a part of a thigh corresponding to an expanse of a femur. Thereby, the thigh retaining member is enabled to retain the entire thigh both firmly and evenly so that a force can be effectively transmitted to the thigh without causing discomfort to the wearer. This effect can be particularly enhanced when the thigh retaining member is connected to the thigh support member in a rotatable and axially slidable manner.

To facilitate the wearing of the thigh retaining member to the thigh of the wearer and, at the same time, to securely keep the thigh retaining member on the thigh of the wearer, a width W1 of a space between free ends of the arms is smaller than an inner diameter W2 of the thigh retaining member in a natural state of the thigh retaining member.

BRIEF DESCRIPTION OF THE DRAWINGS

Now the present invention is described in the following with reference to the appended drawings, in which.

DETAILED DESCRIPTION OF THE PREFERRED EMBODIMENTS

Figure 1:
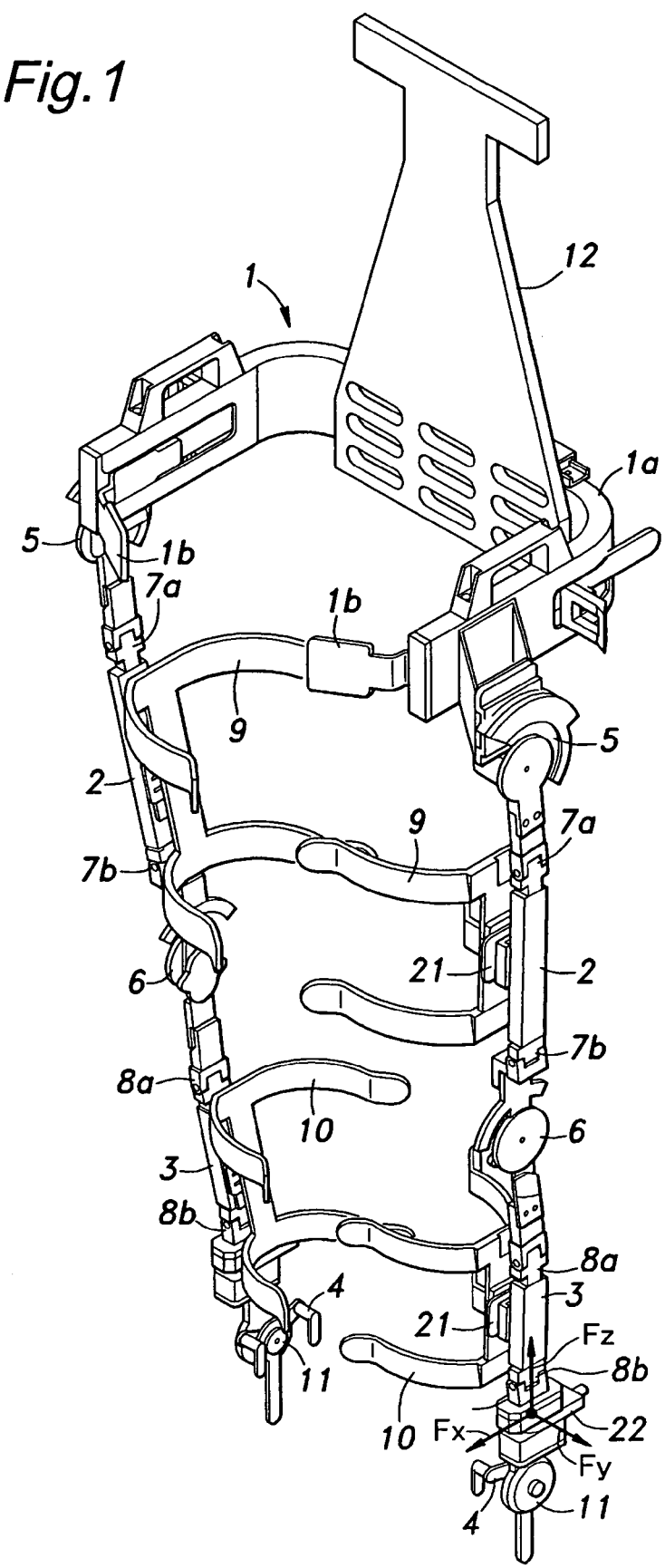
FIG. 1 is an overall perspective view of the walking assistance device embodying the present invention.
Figure 2:
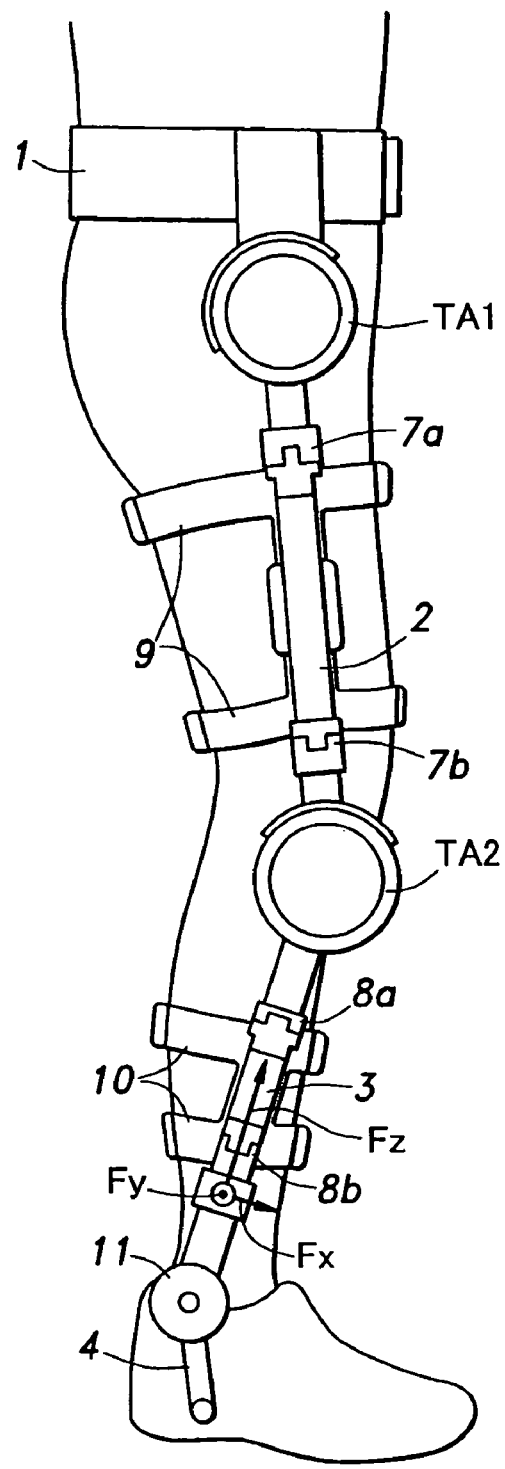
FIG. 2 is a side view showing the walking assistance device as worn by a person.

FIG. 1 is an overall perspective view of an exoskeltal walking assistance device embodying the present invention, and FIG. 2 is a side view showing the walking assistance device when worn by a user. As shown in FIG. 1, the walking assistance device comprises a pelvis support member 1 adapted to be worn on the pelvis of the user, a thigh support member 2 which is vertically elongated so as to be placed on the outer side part of each thigh of the user, a leg support member 3 adapted to be placed on the outer part of each leg of the user, and a foot support member 4 adapted to be engaged by the shoe worn on each foot of the user. The "thigh" as used herein means a part of the limb extending between the hip joint and knee joint, and the "leg" as used herein means a part of the limb extending between the knee joint and ankle.

Figure 3:
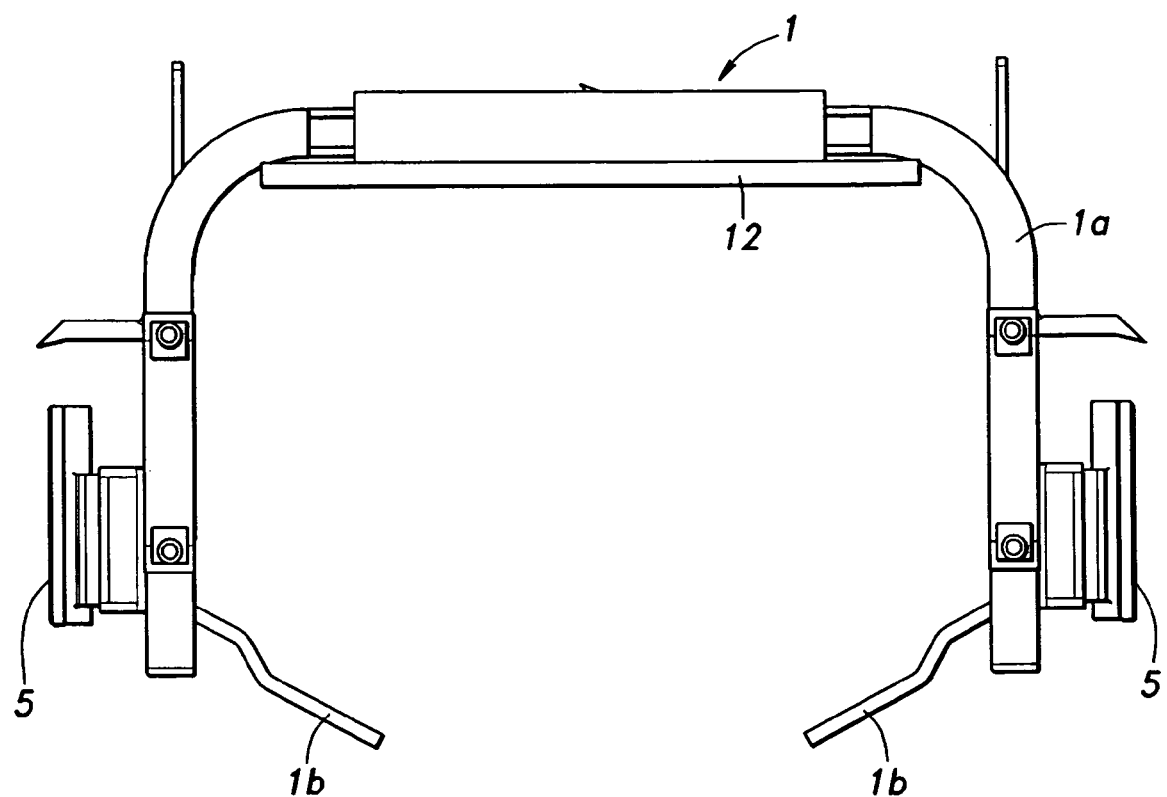
FIG. 3 is an enlarged plan view of the pelvis support member.

As shown in FIG. 3, the pelvis support member 1 includes a base portion 1a made of a relatively rigid material and provided with the shape of letter-U as seen in plan view and a pair of flaps 1b each extending from a corresponding open front end of the base portion 1a and made of a resilient thin plate member so that the pelvis support member 1 presents the shape of letter-C including an open central front part in plan view. The middle part of the base portion 1a is configured to be extended laterally and selectively fixed in length by using a fastener such as a threaded bolt once the base portion 1a is extended to a length that fits the particular user.

The front end of each side portion of the pelvis support member 1 is provided with a pelvis actuator base 5 for mounting a first torque actuator TA1 (FIG. 2) for applying a torque to the pelvic joint of the corresponding side. The output end of the first torque actuator TA1 is connected to the upper end of the thigh support member 2. The lower end of each thigh support member 2 is provided with a knee actuator base 6 for mounting a second torque actuator TA2 (FIG. 2) for applying a torque to the knee joint of the corresponding side. The output end of the second torque actuator TA2 is connected to the upper end of the leg support member 3.

The thigh support member 2 is joined to the output end of the first torque actuator TA1 and knee actuator base 6, in each case, in an articulated manner via a hinge 7a, 7b having a hinge axis extending in the fore-and-aft direction. The leg support member 3 is joined to the output end of the second torque actuator TA2 and foot support member 4, in each case, in an articulated manner via a hinge 8a, 8b having a hinge axis extending in the fore-and-aft direction. The thigh support member 2 and leg support member 3 are each adapted to be extended in length and fixed in length once the length is adjusted so as to suit the build of the wearer by using a fastener such as a threaded bolt.

Each of the torque actuators TA1, TA2 consists of an electric motor fitted with a clutch and a reduction gear, and the motor housings thereof are mounted on the actuator bases 5, 6 provided on the pelvis support member 1 and the lower end of the thigh support member 2, respectively, while the output ends or rotors thereof are fixedly connected to the upper ends of the thigh support member 2 and leg support member 3, respectively. Thereby, an assisting torque corresponding to the intended movement of each of the hip joint (the joint between the pelvis support member 1 and thigh support member 2) and knee joint (the joint between the thigh support member 2 and leg support member 3) is produced. The torque actuators TA1 and TA2 are mounted on the actuator bases 5 and 6, respectively, by using fasteners such as threaded bolts that can be fastened and unfastened repeatedly for the convenience of the servicing the torque actuators TA1 and TA2.

Each thigh support member 2 is provided with a thigh retaining member 9 which is mounted at a suitable point on the thigh support member 2 in a vertically slidable manner, and adapted to attach the thigh support member 2 to the thigh of the wearer. Each leg support member 3 is similarly provided with a leg retaining member 10 which is mounted at a suitable point on the leg support member 3 in a vertically slidable manner, and is adapted to attach the leg support member 3 to the leg of the wearer. If desired, the thigh retaining member 9 and/or the leg retaining member 10 may be rotatable relative to the thigh support member 2 and/or the leg support member 3, respectively.

The joint 11 between each leg support member 3 and corresponding foot support member 4 is rotatable around a laterally extending axis so as to accommodate the normal movement of the ankle.

To a central part of the pelvis support member 1 is attached a back plate 12 for mounting auxiliary equipment not shown in the drawings. For instance, a control circuit and a battery are mounted on the back plate 12.

Figure 6:
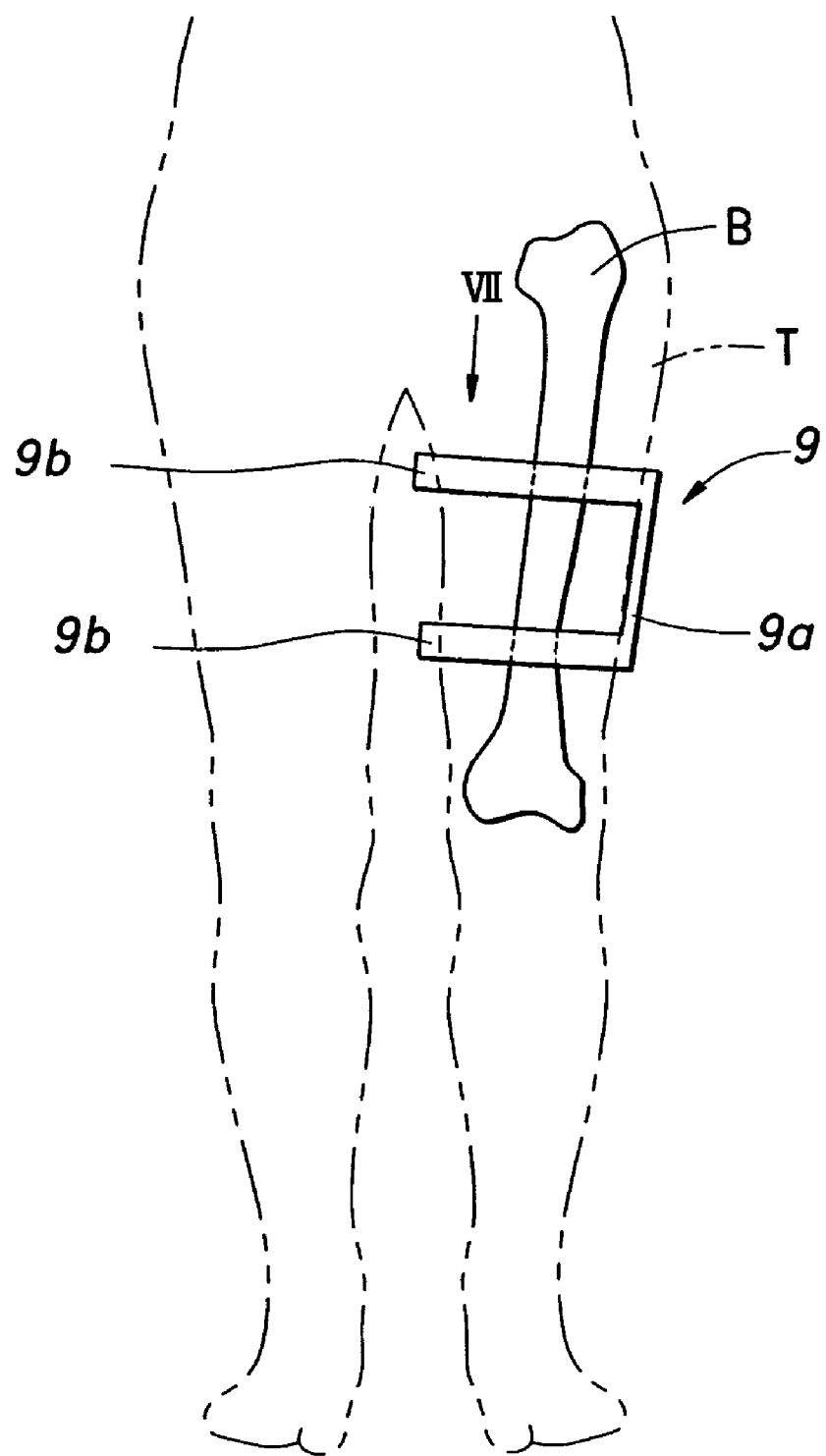
FIG. 6 is a schematic view showing how the thigh retaining member is worn on the thigh of the user.
Figure 7:
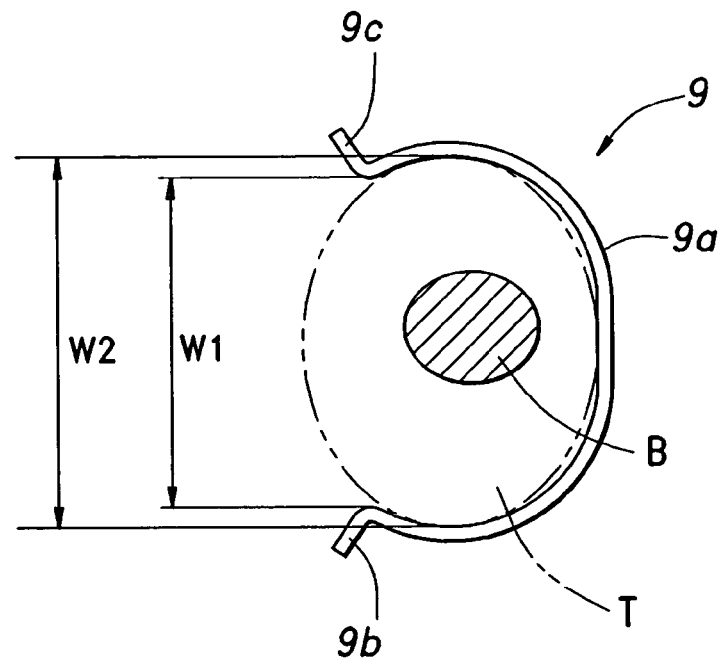
FIG. 7 is an end view of the thigh retaining member as seen in the direction indicated by arrow VII in FIG. 6.

The thigh retaining member 9 is described in the following in more detail with reference to FIGS. 5 to 7. The term "rigidity" as used hereinafter means the "rigidity against bending deformation" of the thigh retaining member when subjected to a bending stress by an assisting torque that is transmitted from the hip joint actuator to the thigh via the thigh support member 2.

Figure 5:
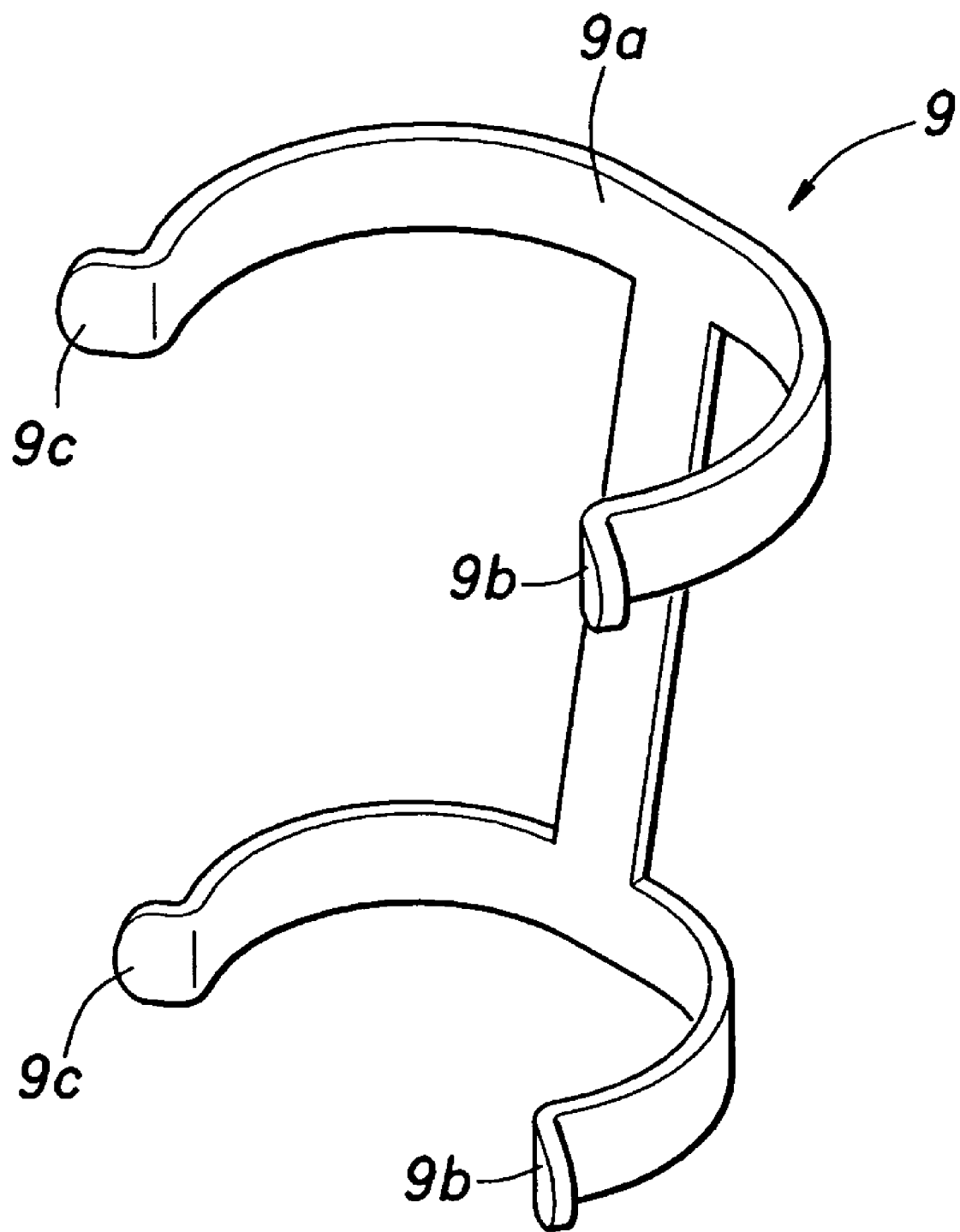
FIG. 5 is an enlarged perspective view of the thigh retaining member.

As best shown in FIG. 5, the thigh retaining member 9 comprises a base portion 9a having a vertically elongated rectangular configuration and adapted to be applied to a laterally outer side of the thigh and two pairs of resilient arms 9b and 9c, one pair extending laterally from either side of an upper end of the base portion 9a and the other pair extending laterally from either side of a lower end of the base portion 9a. Each pair of resilient arms 9b and 9c define a shape of letter-C in plan view in cooperation with the base portion 9a. The free end of each arm 9b and 9c is curved outward so that the arms 9b and 9c may deform outwardly away from each other when the thigh retaining member 9 is pushed against the outer lateral side of the thigh and the wearing of the thigh retaining member 9 may be thereby facilitated. Once the thigh retaining member 9 is worn on the thigh, as illustrated in FIGS. 6 and 7 the thigh retaining member 9 closely surrounds the thigh except for a small gap between the free ends of the arms which is narrower than the diameter of the thigh.

The rigidity of the base portion 9a is selected to be relative high so that the assisting torque provided by the actuator may be transmitted to the entire part of the thigh evenly and a required amount of assisting torque may be transmitted to the thigh. The "entire part of the thigh" as used herein means at least the part of the thigh T including the femur or thigh bone as shown in FIGS. 6 and 7. If the base portion 9a has a relatively large surface area, the pressure that is applied to the thigh T is spread over the large area and the comfort of the wearer can be improved.

The rigidity of the arms 9b and 9c is selected to be relatively low so that the arms may be able to resiliently bend away from each other. The rigidity is selected in such a manner that the arms can be bent outward by hand. Because the free ends of the arms are curved outward, the user can hold the free ends of the arms even when the arms are placed around the thigh. The space W1 between the free ends of the arms in a free state is narrower than the diameter or width W2 of the thigh T as shown in FIG. 5.

The base portion 9a and arms 9b and 9c may be made of a single piece fiber-reinforced composite member, or, alternatively, the arms may be made separately from the base portion and attached thereto by using a fastener or bonding agent. Typically, the fiber-reinforced composite material is prepared by impregnating reinforcing fibers such as carbon fibers, glass fibers and aramid fibers with thermosetting plastic material such as epoxy, bismaleimide and phenol resins or thermoplastic plastic material such as PEEK, nylon-6, nylon-66 and polyethylene terephthalate resins. Particularly when the thigh retaining member 9 is entirely made of a single piece fiber-reinforced composite member, the weight of the thigh retaining member 9 can be minimized, and this improves the comfort of the wearer. However, it is also possible to use other materials for the thigh retaining member and form the thigh retaining member from a plurality of members that are suitable joined to each other according to a broad concept of the present invention.

Also, when fiber-reinforced composite material is used, it is possible to increase the rigidity of the base portion 9a while increasing the flexibility of the arms 9b and 9c by suitably selecting the orientation angle (relative to the circumferential direction), number of lamination layers and density of the reinforcing fibers. For instance, the density of the reinforcing fibers may be increased and/or the number of lamination layers may be increased in the base portion 9a and the density of the reinforcing fibers may be decreased and/or the number of lamination layers may be decreased in the arms 9b and 9c to achieve such a distribution of rigidity in the thigh retaining member 9.

The arms may be provided only in the upper and lower ends of the base portion 9a. This can be achieved either by forming the thigh retaining member 9 as having such a shape or by forming a part-cylindrical hollow member and cutting it into the final shape of the thigh retaining member 9. Therefore, even when the thigh retaining member 9 is formed as a single piece or multi-piece member having a relatively uniform constitution, it can be given with a relatively rigid base portion and relatively flexible arms on account of such a shape of the thigh retaining member 9. The "uniform constitution" as used herein means that the orientation angle of the reinforcing fibers, number of lamination layers and density of the fiber reinforce composite material are uniform.

The arms 9b and 9c may each have a same (vertical) width as is the case in the illustrated embodiment, but may also each have a tapering width. For instance, the base end of each arm may be vertically wider at a base end and narrower at a free end. In this case also, without regards if the thigh retaining member 9 is made of fiber reinforce composite material of uniform or non-uniform constitution, it is possible to make the base portion relatively rigid and arms relatively flexible.

Because the thigh retaining member 9 is provided with an open end defined by the mutually spaced free ends of the arms, the thigh retaining member 9 can be fit on the thigh of the user from the open end thereof and substantially surround the thigh once the thigh retaining member is fit on the thigh. In particular, because the space W1 between the free ends of the arms in a free state is narrower than the diameter or width W2 of the thigh T as shown in FIG. 7, the thigh retaining member 9 can be held in position once it is fit on the thigh of the user. Because the arms are so flexible that the thigh can be pushed into the thigh retaining member 9 and expand the free ends of the arms against the resilient force thereof, and can be removed from the thigh retaining member 9 again by expanding the free ends of the arms against the resilient force thereof. The resiliency of the arms also allow a same thigh retaining member to accommodate a certain range of differences in the diameter of the thigh.

The foregoing description in connection with the thigh retaining member 9 is in most part equally applicable to the leg retaining member 10 which is adapted to be directly worn on the leg of the wearer.

How this walking assistance device can be worn by a user is described in the following. First of all, by resiliently expanding the flaps 1b, the pelvis support member 1 is fitted on the pelvis of the wearer. Once the back plate 12 is brought into contact with the back of the wearer, the flaps 11b are released and allowed to resiliently return to their original shapes. The flaps 1b are thereby resiliently urged against a front part of the pelvis of the wearer, and help the pelvis support member 1 to be held in position on the pelvis of the wearer.

The open end of each of the thigh retaining member 9 and leg retaining member 10 is resiliently expanded and is fitted on the thigh or leg of the wearer. The retaining member is then released in each case, and this places the thigh or leg partly surrounded by the corresponding retaining member 9 or 10. At this time, the clutch of each of the torque actuators TA1 and TA2 may be disengaged so that the torque actuators TA1 and TA2 would not hamper the free movements of the thigh support member 2 and leg support member 3 with respect to the pelvis support member 1 and little effort is required to wear the thigh support member 2 and leg support member 3 on the thigh and leg of the wearer, respectively. Also because the thigh support member 2 and leg support member 3 can bend laterally outward at their upper and lower ends owing to the hinges 7a, 7b, 8a and 8b, the user can wear the walking assistance device 1 without any difficulty even while seated in a chair.

Each retaining member 9 or 10 is joined to the corresponding thigh support member 2 or leg support member 3 in a vertically slidable manner so that each retaining member is allowed to follow the movement of the thigh or leg of the wearer and this enhances the comfort of the wearer.

Figure 4:
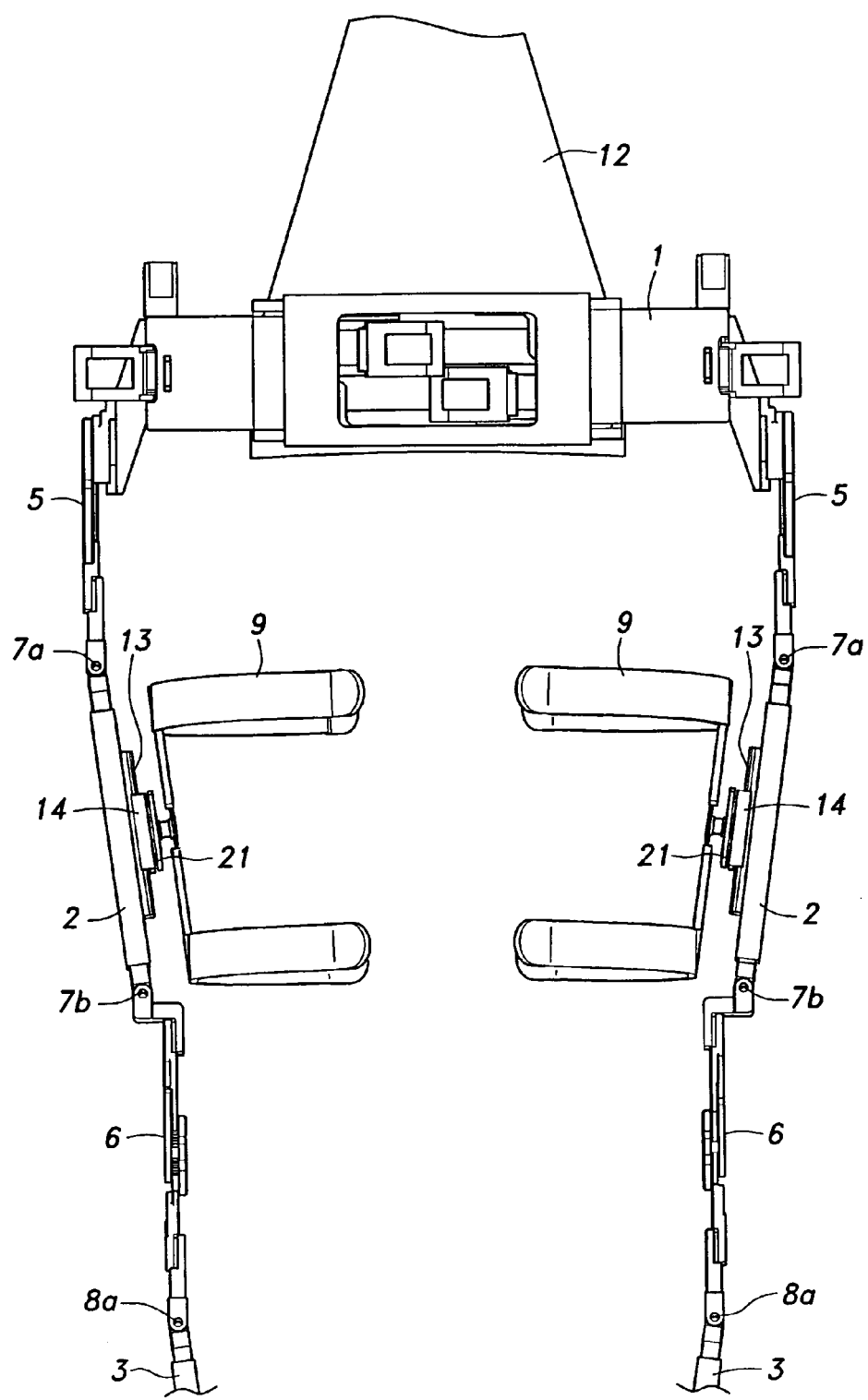
FIG. 4 is a back view of an essential part of the walking assistance device.
Figure 8:
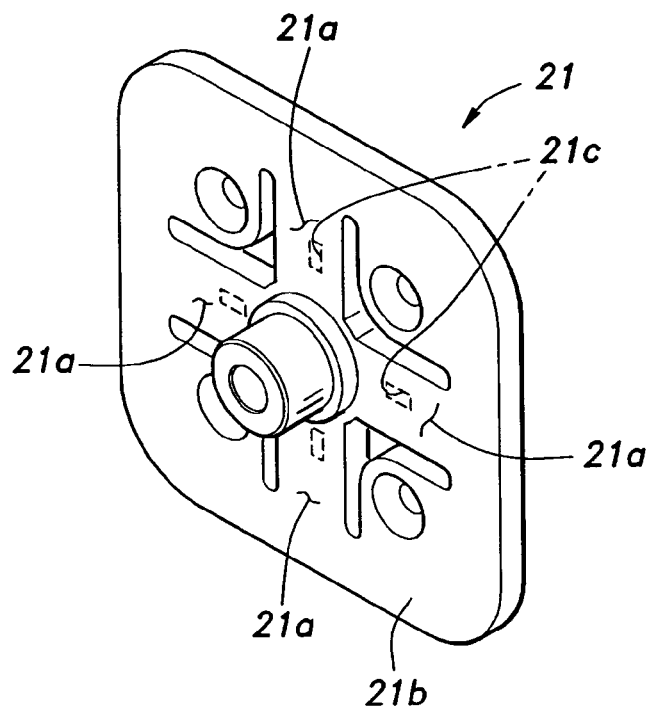
FIG. 8 is a perspective view of the axial force sensor.

As additionally shown in FIG. 4, a tri-axial force sensor 21 is provided in each of the joined parts between the thigh support member 2 and corresponding thigh retaining member 9 and between the leg support member 3 and corresponding leg retaining member 10. As shown in FIG. 8, the axial force sensor 21 is made of a plate member formed with four L-shaped cutouts so as to define a cross shaped portion having four flexible arms 21a and a surrounding rectangular frame portion 21b. This may be formed by machining a plate member made of structural carbon steel, and a strain gage 21c such as a wire resistance strain gage is attached to each of the flexible arms 21a of the cross shaped portion. The base portion of each of the retaining members is attached to the central part of the cross shaped portion at which the flexible arms 21a intersect with each other. The frame portion 21b is fixedly attached to a carriage 14 slidably engaging a guide rail 13 mounted on the thigh support member 2 or leg support member 3, as the case may be.

The force sensor 21 is capable of detecting a composite force that may include vertical, lateral and fore-and-aft components, and is therefore capable of detecting the force acting between the thigh support member 2 and base end of the thigh retaining member 9 or the force acting between the leg support member 3 and base portion of the leg retaining member 10 with respect to all directions.

As shown in FIG. 1, between the leg support member 3 and foot support member 4 is provided a tri-axial sensor 22 which can detect an upward force Fz directed substantially in parallel with the lengthwise direction of the leg support member 3, a forward force Fx perpendicular to the upward force Fz and a laterally outward force Fy perpendicular to the upward force Fz. This tri-axial sensor can detect the magnitude and direction of the force arising from the weight of the walking assistance device worn by the wearer and acting upon the floor surface.

When the wearer swings one of his or her thighs forward around the corresponding hip join, the thigh retaining member 9 receives a force which is directed forward, and this is detected by the force sensor 21. The torque actuator TA1 provided on the corresponding hip joint is actuated in such a manner that this force is canceled, and this causes the thigh support member 2 to follow the movement of the thigh. If the force sensor 21 detects a force even though the wearer is not moving, as it means that the legs of the wearer are supporting the weight of the walking assistance device 1, the torque actuators TA1 and TA2 are actuated in such a manner that the force detected by the tri-axial sensor 22 is minimized. As a result, the weight of the walking assistance device is supported by the soles of the shoes without burdening the legs and thighs of the wearer.

In the foregoing description, the walking assistance device was used for assisting a person suffering from walking impediment owing to the lack of muscle power or for other reasons by using the torques produced from the torque actuators TA1 and TA2. However, the walking assistance device can also be used to applying load to the wearer for the purpose of training the muscles of the wearer. For instance, a person having one of his or her leg suffering from debilitation may use the walking assistance device of the present invention for the purpose of training only the debilitated leg. If required, only one of the actuators TA1 or TA2 may be actuated or the other one may be omitted for the purpose of training only the movement of the wearer around the hip joint or knee joint, as the case may be.

Although the present invention has been described in terms of preferred embodiments thereof, it is obvious to a person skilled in the art that various alterations and modifications are possible without departing from the scope of the present invention which is set forth in the appended claims.

The contents of the original Japanese patent applications on which the Paris Convention priority claim is made for the present application are incorporated in this application by reference.

The invention claimed is:

1. A walking assistance device, including;
   a pelvis support member adapted to be worn by a pelvis of a user;
   a thigh support member having an upper end pivotally connected to the pelvis support member via a hip coupling portion and provided with a thigh retaining member;
   a leg support member having an upper end pivotally connected to a lower end of the thigh support member via a knee coupling portion and provided with a leg retaining member;
   an actuator provided at least in one of the hip coupling portion and knee coupling portion for applying an assisting torque to the two members that are joined by the coupling portion; and
   a force detector provided between the thigh retaining member and thigh support member when the actuator is provided in the hip coupling portion or between the leg retaining member and leg support member when the actuator is provided in the knee coupling portion.

2. The walking assistance device according to claim 1, wherein the actuator is provided in the hip coupling portion to apply an assisting torque between the pelvis support member and thigh support member, and the force detector is provided between the thigh retaining member and thigh support member.

3. The walking assistance device according to claim 2, wherein the thigh support member includes an axially elongated rod member, and the thigh retaining member is connected to the thigh support member in an axially slidable manner.

4. The walking assistance device according to claim 1, wherein the actuator is provided in the knee coupling portion to apply an assisting torque between the thigh support member and leg support member, and the force detector is provided between the leg retaining member and leg support member.

5. The walking assistance device according to claim 4, wherein the leg support member includes an axially elongated rod member, and the leg retaining member is connected to the leg support member in an axially slidable manner.

6. The walking assistance device according to claim 1, wherein the force detector comprises a plate member having a cross shaped part having four arms defined by four L-shaped cuts and a strain sensor attached to each of the four arms.

7. The walking assistance device according to claim 1, further comprising a foot support member having an upper end pivotally connected to a lower end of the leg support member via an ankle coupling portion.

8. The walking assistance device according to claim 7, wherein a force detector is provided in the ankle coupling portion to detect a load acting between the leg support member and foot support member.

9. The walking assistance device according to claim 1, wherein the thigh retaining member comprises a base portion connected to the thigh support member and at least a pair of resilient arms extending laterally from either side of the base portion so that the thigh retaining member generally defines a shape of letter-C in plan view.

10. The walking assistance device according to claim 9, wherein the thigh retaining member comprises two pairs of resilient arms extending laterally from either side of an upper end of the base portion and from either side of a lower end of the base portion, respectively.

11. The walking assistance device according to claim 10, wherein the thigh retaining member is adapted to extend over a part of a thigh corresponding to an expanse of a femur.

12. The walking assistance device according to claim 9, wherein a width W1 of a space between free ends of the arms is smaller than an inner diameter W2 of the thigh retaining member in a natural state of the thigh retaining member.

\* \* \* \* \*